(12) United States Patent
Barnard et al.

(10) Patent No.: US 6,252,024 B1
(45) Date of Patent: Jun. 26, 2001

(54) FLUORESCENT N-ALKYLATED ACRYLAMIDE COPOLYMERS AND OPTICAL PH SENSORS

(75) Inventors: Steven Mark Barnard, Wellesley Hills, MA (US); Joseph Berger, Muttenz (CH); Marizel Rouilly, Gipf-Oberfrick (CH); Adrian Waldner, Allschwil (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/051,496

(22) PCT Filed: Oct. 11, 1996

(86) PCT No.: PCT/EP96/04426

§ 371 Date: Nov. 2, 1998

§ 102(e) Date: Nov. 2, 1998

(87) PCT Pub. No.: WO97/15832

PCT Pub. Date: May 1, 1997

(30) Foreign Application Priority Data

Oct. 23, 1995 (CH) .................................................. 2995/95

(51) Int. Cl.$^7$ ........................ C08F 226/06; C08F 224/00
(52) U.S. Cl. ........................ 526/259; 526/267; 526/281
(58) Field of Search ................................. 526/259, 267, 526/268, 281, 284

(56) References Cited

U.S. PATENT DOCUMENTS

| 4,716,118 | 12/1987 | Wolfbeis et al. . | |
|---|---|---|---|
| 4,898,691 | 2/1990 | Borzo et al. . | |
| 5,132,057 | 7/1992 | Tomisaka et al. . | |
| 5,273,716 | 12/1993 | Northrup et al. . | |
| 5,521,269 | * 5/1996 | Miyashita | 526/259 |
| 5,986,030 | * 11/1999 | Murray | 526/268 |

* cited by examiner

Primary Examiner—Christopher Henderson
(74) Attorney, Agent, or Firm—Wenderoth, Lind & Ponack, L.L.P.

(57) ABSTRACT

A water-insoluble copolymer which is composed of (a) from 39.9 to 60% by weight of N,N-dimethylacrylamide or N,N-dimethylmethacrylamide; (b) from 60 to 39.9% by weight of N-alkylated acryl amides or N-alkylated methacryl amides; (c) from 0.1 to 0.7% by weight of a proton-sensitive fluorophore which is covalently bonded to the copolymer; and (d) from 0 to 20% by weight of a diolefinic crosslinking component. The copolymer is used in the form of a membrane on a transparent support material as an optical sensor for ionic strength-independent pH value determination.

10 Claims, No Drawings

FLUORESCENT N-ALKYLATED ACRYLAMIDE COPOLYMERS AND OPTICAL PH SENSORS

CROSS-REFERENCE TO RELATED APPLICATION

This application is a 371 of PCT/EP96/04426 filed Oct. 11, 1996.

BACKGROUND OF THE INVENTION

1. Field of the Invention

The invention relates to a polymer composition comprising pH-sensitive fluorescent dyes, to an ionic strength-independent optical sensor for pH value determination that contains the composition in the form of a membrane on a transparent support material, and also to an optical process, according to the fluorescence method, that renders possible highly accurate pH value determination independently of the ionic strength of the test solution. The process is especially suitable for the determination of the pH value of physiological solutions, especially for the determination of the pH value of blood.

2. Description of Related Art

It is known that the $pK_a$ value of an indicator varies with the ionic strength of a solution and that that variation depends on the level of the charge at the indicator. For example, it has already been proposed in DE-A-3 430 935 to determine computationally the ionic strength and the pH value from the difference between the measured values of two sensors having different ionic strength dependence of which one exhibits as low as possible an ionic strength dependence, after calibration of said sensors with known test solutions. The sensor described therein that is almost independent of the ionic strength does not lie exactly within the physiological pH range and has a low resolution. The construction of those sensors is effected without embedding into a polymer matrix and consequently has the disadvantage that the dye is in direct contact with the test solution. The fluorescent dye of the sensors, which is the same in each case, is in that arrangement immobilised directly on the surface of glass supports by way of bridging groups, one of the sensors containing additional charges for achieving a high polarity and ionic strength dependence and the other sensor being so modified that it is essentially non-polar, hydrophobic and independent of the ionic strength. A quite considerable disadvantage of those sensors is that the fluorescent dye is exposed directly to external influences of the test solutions, and both physical influences (for example dissolution of the dye, deposits on the surface) and chemical influences (decomposition of the dye) quickly make the sensors unusable. In addition, in the case of excitations in an evanescent field, interference between the evanescent measuring field and the fluorescence of the test sample cannot be completely avoided, which reduces the accuracy of the measurement. The response time of those sensors is on the other hand short, since the fluorescent dye bonded to the surface immediately comes into contact with the test solution. The sensitivity is regarded as adequate.

The method of optical pH determination using two sensors that respond to different extents to the ionic strength of a test solution is expensive in respect of apparatus and a subsequent, additional calculation step has to be carried out.

BRIEF SUMMARY OF THE INVENTION

It has now been found that, by selection of quite specific copolymers of acrylamides and methacrylamides in conjunction with the selection of a narrow concentration range of a fluorescent dye, which is embedded in the polymer matrix, it is possible to produce an optical pH sensor that allows highly accurate optical pH measurement that is independent of ionic strength in the physiological pH range of from 6.5 to 8.2. By that means, a second measurement and the calculation step for eliminating the ionic strength are dispensed with. The high degree of accuracy of the pH value measurement is of great importance especially in the analysis of human blood, since the measurement can be used, for example, for monitoring the therapy of metabolic diseases. For a quick and inexpensive test it is therefore especially advantageous if only one sensor has to be used. The analytical apparatus can consequently also be miniaturised more easily.

DETAILED DESCRIPTION OF THE INVENTION

The shelf life and working life of those sensors is high since the fluorescent dye is effectively protected by the polymer matrix against damaging or interfering influences of the test medium. The sensitivity is not reduced in such sensors and the response times are surprisingly short.

By means of the polymer compositions it is possible to set very accurately, for example, the hydrophilic property, hydrophobic property, polarity and/or dielectric constant of the matrix, which, combined with the selected concentration range of the fluorophore, results in a measurement that is independent of ionic strength within a particular pH value range.

The response times and the conditioning times correspond to the short periods of time required of optical measuring systems despite embedding of the fluorophore, those parameters being dependent essentially on the membrane thickness.

The invention relates to water-insoluble copolymers that are composed of
a) from 39.9 to 60% by weight of N,N-dimethylacrylamide or N,N-dimethylmethacrylamide;
b) from 60 to 39.9% by weight of a monomer of formula Ia or Ib

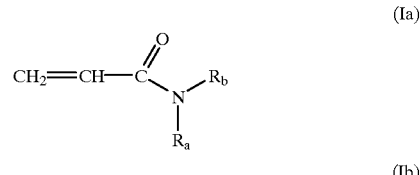

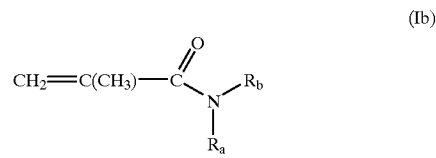

wherein $R_a$ is hydrogen or $C_1$–$C_6$alkyl and Rb is $C_1$–$C_{12}$alkyl; with the proviso that $R_a$ and $R_b$ are not both methyl;
c) from 0.1 to 0.7% by weight of a proton-sensitive fluorophore which is covalently bonded to the polymer; and
d) from 0 to 20% by weight of a diolefinic crosslinking component, the sum of the percentage weights of a) to d) being 100%.

Within the scope of the present invention, "water-insoluble" denotes that at most traces of less than 0.1% are able to dissolve. In order, on the other hand, to be able to produce a good contact with the test medium, the copolymer must, however, be swellable. The alkyl radicals may be linear or branched. Examples of $C_1$–$C_{12}$alkyl are the linear or branched radicals: methyl, ethyl and the various position isomers of propyl, butyl, pentyl, hexyl, heptyl, octyl, nonyl, decyl, undecyl or dodecyl.

The monomer preferably used as monomer a) is N,N-dimethylacrylamide.

Preferred water-insoluble copolymers are obtained when $R_a$ is hydrogen and $R_b$ is a branched $C_3$–$C_8$alkyl. Especially preferred are water-insoluble copolymers in which $R_a$ is hydrogen, $R_b$ is tertiary butyl and the ratio of monomer a) to monomer b) is 50 parts by weight to 50 parts by weight.

Another group of preferred water-insoluble copolymers is obtained when $R_a$ is methyl or ethyl and $R_b$ is linear $C_3$–$C_8$alkyl. Especially preferably, $R_a$ is methyl and $R_b$ is n-butyl.

Suitable proton-sensitive fluorescent dyes are, for example, those from the group of the xanthenes and benzoxanthenes, for example fluorescein, halogenated fluoresceins, seminaphthofluoresceins, seminaphthorhodafluors, 2,3-benzo fluorescein, 3,4-benzofluorescein, the isomers of benzorhodamine and substituted derivatives, the isomers of benzochromogen and substituted derivatives; acridines, for example acridine, 9-amino-6—chloroacridine; acridones, for example 7-hydroxyacridone and 7-hydroxybenz acridone; pyrenes, for example 8-hydroxypyrene-1,3,6-trisulfonic acid; cyanine dyes; and coumarins, for example 7-hydroxycoumarin and 4-chloromethyl-7-hydroxycoumarin. The fluorescent dyes may be functionalised with olefinically unsaturated groups in order to bind to the polymer backbone.

Preferably, the fluorophores are selected from the group consisting of acridines, acridones, rhodamines, xanthenes, benzoxanthenes, pyrenes and coumarins, which are either admixed with or covalently bonded to the polymer.

Preferred are water-insoluble copolymers in which the flourophore is covalently bonded to the polymer.

Especially preferred are water-insoluble copolymers in which the fluorophore is a compound of formula II, III, IV, V or VI

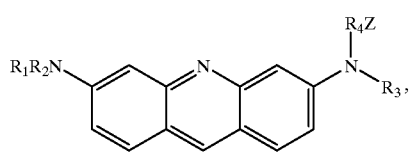

(II)

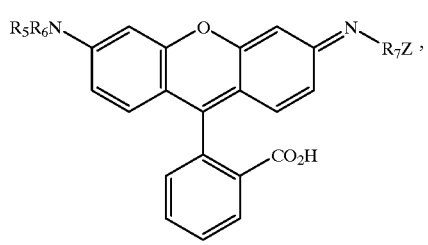

(III)

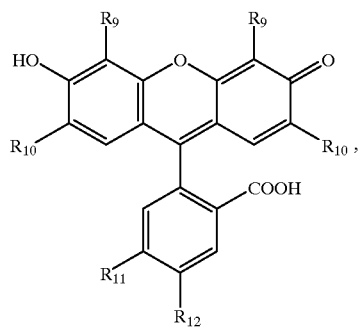

(IV)

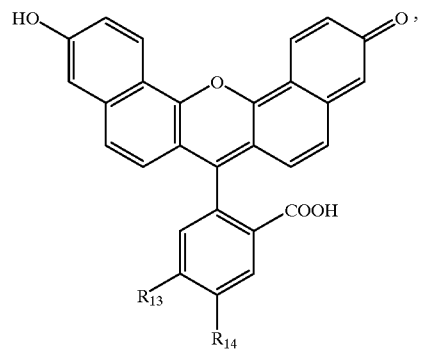

(V)

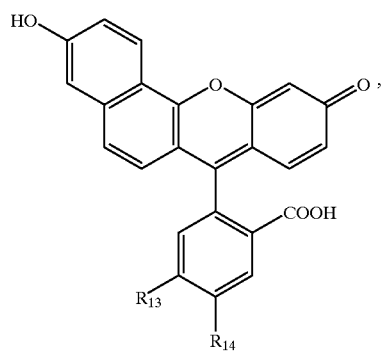

(VI)

wherein
$R_1$, $R_2$, $R_5$ and $R_6$ are each independently of the others hydrogen, —$SO_2$—($C_1$–$C_6$)alkylphenyl, $C_1$–$C_{30}$alkyl, $C_1$–$C_{30}$alkyl-CO— or a radical of the formula —($C_nH_{2n}$—O—$)_m$—$R_8$;
$R_3$ is hydrogen or —$SO_2$—($C_1$–$C_6$)alkylphenyl;
$R_4$ and $R_7$ are a $C_1$–$C_{30}$alkylene or a radical of the formula —($C_nH_{2n}$—O—$)_m$—$R_8$;
Z is a divalent radical —NH—CO—;
$R_8$ is a direct bond or $C_1$–$C_{12}$alkylene;
n is an integer from 2 to 6 and m is an integer from 1 to 10, with the proviso that the total number of carbon atoms is no more than 30;
$R_9$ and $R_{10}$ are each independently of the other H, $C_1$–$C_4$alkyl, $C_1$–$C_4$alkoxy, $C_1$–$C_4$alkoxycarbonyl, $C_1$–$C_4$alkyl-$SO_2$— or halogen, and either
$R_{11}$ is H and $R_{12}$ is a divalent radical —NH—CO—, —CO—NH—($C_2$–$C_{12}$alkylene-O)—CO—, —CO—NH—($C_2$–$C_{12}$alkylene-NH)—CO— or —C(O)—NH—($CH_2CH_2$-O$)_{1'}$ to $_6$-$CH_2$C(O)—NH—, or $R_{11}$ is a divalent radical —NH—CO—, —CO—NH—($C_2$–$C_{12}$alkylene-O)—CO—, —CO—NH—($C_2$–$C_{12}$alkylene-NH)—CO— or —C(O)—NH—(CH$_2$CH$_2$—O)$_1$ to $_6$-CH$_2$C(O)—NH—, and R$_{12}$ is H; or wherein either R$_{13}$ is H and R$_{14}$ is a divalent radical —NH—C(O)—, —CO—NH—(C$_2$-C$_{12}$alkylene-O)—CO—, —CO—NH—(C$_2$-C$_{12}$alkylene-NH)—CO— or —C(O)—NH—(CH$_2$CH$_2$—O)$_1$ to $_6$-CH$_2$C(O)—NH—, or R$_{13}$ is a divalent radical —NH—C(O)—, —CO—NH—(C$_2$-C$_{12}$alkylene-O)—CO—, —CO—NH—(C$_2$-C$_{12}$alkylene-NH)—CO— or —C(O)—NH—(CH$_2$CH$_2$—O)$_1$ to $_6$-CH$_2$C(O)—NH—, and R$_{14}$ is H, wherein the radical —COOH is each in free form or in salt form, or a C$_1$-C$_{20}$ alkyl ester thereof.

Alkyl as such or as a structural element of other groups, such as, for example, of alkoxy and alkoxycarbonyl is, with appropriate consideration given in each case to the number of carbon atoms respectively included in the corresponding group or compound, either straight-chain, that is to say methyl, ethyl, propyl or butyl, or branched, e.g. isopropyl, isobutyl, sec-butyl or tert-butyl.

Halogen is fluorine, chlorine, bromine or iodine, especially fluorine, chlorine or bromine, more especially chlorine or bromine.

Examples from which the divalent radicals Z, R$_{11}$, R$_{12}$, R$_{13}$ and R$_{14}$ may arise are the acryloylamine group —NHCOCH═CH$_2$, the methacryloylamine group —NHCOC(CH$_3$)═CH$_2$, and the 2-(methacryloyloxy)-ethylaminocarbonyl group —CONHCH$_2$CH$_2$OCOC(CH$_3$)═CH$_2$.

Preferably, R$_1$ and R$_2$ of the fluorophore of formula II are each independently of the other hydrogen or linear C$_{12}$–C$_{24}$alkyl.

Also preferably, R$_4$ of the fluorophore of formula II is a linear C$_2$–C$_{16}$alkylene or a radical of the formula —(C$_2$H$_4$—O—)$_m$—R$_8$ wherein R$_8$ and m are as defined hereinbefore.

Another group of preferred water-insoluble copolymers is formed by those in which R$_5$ and R$_6$ of the fluorophore of formula III are each independently of the other linear C$_2$–C$_{12}$alkyl.

Copolymerisable fluorescent dyes contain, for example, an ethylenically unsaturated group (vinyl, crotonyl, methallyl) that is bonded directly or via a bridging group to the fluorescent dye. The monomers a) and b) are known. A known copolymerisable fluorescent dye is, for example, 3- or 4-acryloylaminofluorescein.

Polymers with fluorescent dyes comprising the bridging groups —O—C(O)— and —C(O)—O—C$_2$–C$_{12}$alkylene-O—C(O)— are obtainable, for example, by esterification with fluorescent dyes that contain carboxyl or hydroxyl groups. Polymers with fluorescent dyes comprising the bridging groups —NH—C(O)—O— and —NH—C(O)—O—C$_2$–C$_{12}$alkylene-O—C(O)— are accessible, for example, by way of isocyanate-functionalised fluorescent dyes and hydroxyl group-containing polymers.

The reactions described above may be carried out in a manner known per se, for example in the absence or presence of a suitable solvent, as required with cooling, at room temperature or with heating, e.g. in a temperature range of from approximately 50° C. to approximately 200° C., preferably approximately from 20° C. to 120° C., and, if necessary, in a closed vessel, under pressure, in an inert gas atmosphere and/or under anhydrous conditions.

The preparation of the polymers may be carried out according to methods known per se.

The reactants may be reacted with one another as they are, that is to say without the addition of a solvent or diluent, e.g. in the melt. Generally, however, the addition of a solvent or diluent or of a mixture of solvents is advantageous. There may be mentioned as examples of such solvents and diluents: water; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxy diethyl ether, tetrahydrofuran or dioxane; ketones, such as acetone, methyl ethyl ketone or methyl isobutyl ketone; alcohols, such as methanol, ethanol, propanol, isopropanol, butanol, ethylene glycol or glycerol; amides, such as N,N-dimethylformamide, N,N-diethylformamide, N,N-dimethylacetamide, N-methylpyrrolidone or hexamethylphosphoric acid triamide; nitriles, such as acetonitrile or propionitrile; and sulfoxides, such as dimethyl sulfoxide.

The copolymerisable fluorescent dyes may be prepared according to processes known per se, and the starting materials are either available commercially or can be prepared according to analogous processes.

One possible method of preparing compounds of formula II or III comprises a) in compounds of formula IIc or IIIc

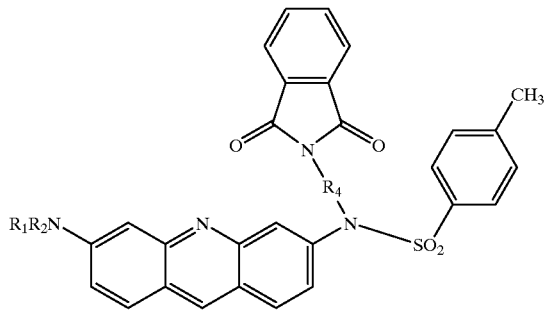

(IIc)

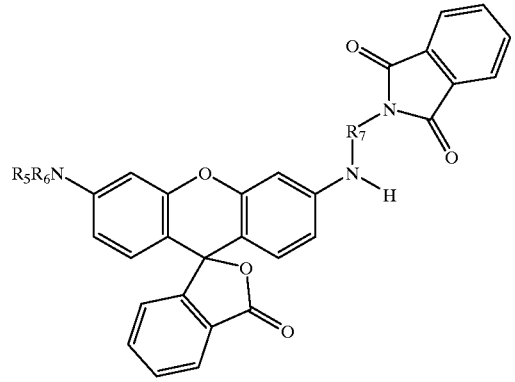

(IIIc)

removing the phthalimide group under acidic conditions and, where appropriate, in a second step b) further reacting the reaction products with acrylic acid chloride or methacrylic acid chloride or c) where appropriate, removing the para-toluenesulfonyl group from the reaction products of the starting materials of formula Hl under acidic conditions, the radicals R$_1$, R$_2$, R$_4$, R$_5$, R$_6$ and R$_7$ being as defined hereinbefore.

The methods for the removal of the protecting groups are known per se and may be used in an analogous manner in the preparation of the compounds of formulae II and III.

The compounds of formula IIc can be prepared in a manner known per se by stepwise alkylation with different alkylating agents, or alkylation with an alkylating agent or acylating agent of commercially available 3,6-diaminoacridine. Suitable alkylating agents are, for example, dialkyl sulfates or monohaloalkanes, especially chloro-, bromo- and iodo-alkanes. Suitable acylating agents are, for example, carboxylic acid anhydrides and, especially, carboxylic acid halides, such as, for example, carboxylic acid chlorides. That reaction may be carried out in the presence of inert polar and aprotic solvents, for example ethers, alkylated acid amides and lactams or sulfones, and at elevated temperatures, for example from 50 to 150° C. Expediently, a hydrogen halide acceptor is added, for example an alkali metal carbonate or a tertiary amine, especially a sterically hindered tertiary amine.

The compounds of formula IIIc are obtainable, for example, by the reaction of phthalic acid anhydride with 2 molar equivalents of 3-monoalkylaminophenol. Another possible method of preparation is the reaction of 3-monoalkylaminophenol with one molar equivalent of 2-hydroxy-4-dialkylamino-2'-carboxyl-benzophenone. Those reactions are described, for example, in U.S. Pat. No. 4,622,400.

Compounds of formulae IV, V and VI may be prepared in an analogous manner.

Conditions for the reactions are known per se. They may be carried out, for example, in the presence of a suitable solvent or diluent or a mixture thereof, as required with cooling, at room temperature or with heating, e.g. in a temperature range of from approximately −10° C. to the boiling temperature of the reaction mixture, preferably from approximately 0° C. to approximately 25° C., and, if necessary, in a closed vessel, under pressure, in an inert gas atmosphere and/or under anhydrous conditions. Especially advantageous reaction conditions are disclosed in the Examples.

Preferably, the copolymers have a mean molecular weight of from 2 000 to 500 000, especially from 10 000 to 350 000 daltons, determined acording to the gel permeation method using standard polymers of known molecular weight.

The water-insoluble copolymers may be crosslinked in the form of a layer, for example with from 0.01 to 20%, preferably from 0.1 to 10%, and especially preferably from 0.5 to 5%, by weight of a crosslinking agent based on the polymer. Suitable crosslinking agents are, for example, acrylic acid or methacrylic acid esters or amides of polyols, preferably diols to tetrols, or polyamines, preferably diamines to tetramines. Such crosslinking agents are known and widely described in the literature. Some examples of polyols are ethylene glycol, 1,3-propanediol, 1,4-butanediol, 1,6-hexanediol, diethylene glycol, 1,1,1-trihydroxymethyl ethane or propane, pentaerythritol and dipentaerythritol. Some examples of polyamines are ethylenediamine, 1,3-propanediamine, 1,4-butanediamine, 1,6-hexanediamine, diethylenetriamine and triethylenetetramine. Another known crosslinking agent is, for example, divinylbenzene. Alkylene-bis-dialkylmaleimidyl compounds, for example, are also suitable, for example ethylene-bis-(dimethyl) maleimidyl.

The invention relates also to a composition and to an optical sensor for an ionic strength-independent determination of pH value, consisting of
A) a transparent support material
B) a layer of water-insoluble copolymers that are composed of
a) from 39.9 to 60% by weight of N,N-dimethylacrylamide or N,N-dimethylmethacrylamide;
b) from 60 to 39.9% by weight of a monomer of formula Ia or Ib

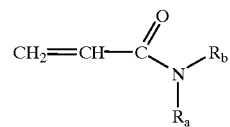

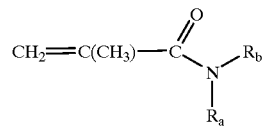

wherein $R_a$ is hydrogen or $C_1$–$C_6$alkyl and $R_b$ is $C_1$–$C_{12}$alkyl; with the proviso that $R_a$ and $R_b$ are not both methyl;
c) from 0.1 to 0.7% by weight of a proton-sensitive fluorophore which is covalently bonded to the polymer; and
d) from 0 to 20% by weight of a diolefinic crosslinking component,
the sum of the percentage weights of a) to d) being 100%.

The copolymer and fluorescent dye preferences given above apply likewise to the sensor.

Sensors in which the fluorophore is admixed with the polymer are suitable principally for once-only use. If the polymer membrane is provided with a permeable and hydrophilic protective layer, then both those sensors and also, in general, sensors with polymer-bonded fluorophores, which may also contain a protective layer on the membrane, may be used repeatedly or for continuous measurements.

The geometric form of the support material may vary widely; it may be, for example, fibres, cylinders, spheres, cuboids or cubes. Furthermore, flow systems in which continuous measurements or successive measurements may be carried out are possible. Planar sensors are preferred. The support material is transparent. It may be, for example, inorganic glass or transparent plastics, such as a polycarbonate, a polyester (for example polyethylene erephthalate), a polyamide, or a polyacrylate or polymethacrylate.

The planar sensor may be of any external shape, for example square, rectangular or round. It may have a surface area of from 0.01 to approximately 50 cm², more advantageously from 0.02 to 10 cm². The measuring zone of the sensor may have a surface area of less than 5 mm², preferably less than or equal to 2 mm². The measuring zone may be correspond exactly to one completely coated surface of the sensor. Advantageously, a coating that is on both sides but that is locally separated may be used.

The sensor may comprise one or more locally separated membrane layers; in the latter case parallel measurements may be carried out with identical or different test samples.

Preferably, the thickness of the polymer layer B) is from 0.1 to 500 μm, especially preferably from 1 to 100 μm.

The production of such layers can be carried out in a manner known per se, for example by dissolving the composition in an organic solvent, then casting to form a film and finally removing the solvent.

Also possible for the production of the layers are processes known from coating technology.

Examples are spin-coating, spraying or knife application processes, with spin-casting processes being preferred.

Suitable solvents include alcohols, ethers, esters, acid amides and ketones. Especially suitable are readily volatile solvents, especially tetrahydrofuran.

In addition to those processes, in which the composition is first of all dissolved, moulded and the solvent subsequently evaporated again, hot-moulding processes are also possible, since the composition is a thermoplastic material. Suitable processes include extrusion, injection moulding, pressing or blowing processes as known from thermoplastic plastics processing.

The layer may be transparent or slightly opaque. Preferably it is transparent.

In order to improve the adhesion, the support materials may be treated beforehand with adhesion promoters. For the same purpose, a plasma treatment of the support material in order to produce functional groups on the surface is also possible. The surface may also be provided with copolymerisable groups in order to achieve an especially high level of adhesion. Known adhesion promoters for glasses are, for example, triethoxy-glycidyloxysilane, 3-azidopropyl-triethoxysilane and 3-aminopropyl-triethoxysilane. The thus treated surfaces may be further modified, for example with O—(N-succinimidyl)-6-(4'-azido-2'-nitrophenylamino)-hexanoate.

The invention relates also to a process for the ionic strength-independent, reversible optical determination of the pH value of an aqueous sample according to the fluorescence method, in which process an optical sensor, consisting of A) a transparent support material
B) a layer of water-insoluble copolymers that are composed of
a) from 39.9 to 60% by weight of N,N-dimethylacrylamide or N,N-dimethylmethacrylamide;
b) from 60 to 39.9% by weight of a monomer of formula Ia or Ib

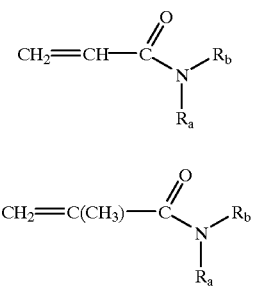

wherein $R_a$ is hydrogen or $C_1$–$C_6$alkyl and $R_b$ is $C_1$–$C_{12}$alkyl; with the proviso that $R_a$ and $R_b$ are not both methyl;
c) from 0.1 to 0.7% by weight of a proton-sensitive fluorophore which is covalently bonded to the polymer; and
d) from 0 to 20% by weight of a diolefinic crosslinking component,
the sum of the percentage weights of a) to d) being 100%, is brought into contact with an aqueous test sample and irradiated with excitation light, the fluorescence is measured, and the pH value is calculated from the measured fluorescence intensity taking calibration curves into consideration.

The above-described preferences in respect of the copolymers and fluorescent dyes apply likewise to the sensor.

In detail, the procedure may be as follows: after calibration with samples of known pH, a measurement of the fluorescence intensity in contact with a test solution of unknown composition is carried out and the pH with respect to the measured fluorescence intensity is determined directly from the calibration.

The sensors are brought into contact with the calibrating solutions and with the test samples. This may be effected by hand (for example by means of pipetting) or using a suitable automatic flow system, the sensors being mounted in fixed position in a flow cell. Such flow cells are known to the person skilled in the art and may be adapted in a simple manner to the purpose in question.

UV lamps (for example mercury vapour lamps, halogen lamps), lasers, diode lasers and light-emitting diodes may be used as light sources for the excitation of the fluorescence. It may be expedient to filter out, by means of filters, light of the wavelength at which the fluorescent dye has an absorption maximum. The fluorescent light emitted by the sensors can be collected, for example using a lens system, and then directed to a detector, for example a secondary electron multiplier or a photodiode. The lens system may be so arranged that the fluorescence radiation is measured through the transparent support, via the edges of the support, or via the analytical sample. Advantageously, the radiation is deflected in a manner known per se by means of a dichroic mirror. The fluorescence of the sensors is measured preferably during contact with the calibrating solutions or sample solutions.

The measurement may be effected under photostationary conditions with continuous illumination, but can, if required, alternatively be time-resolved. This can be achieved, for example, by a laser pulse of limited duration or by modulation of the intensity of a light source.

The response times may be less than 30 seconds and a first measurement is already possible after less than about 5 minutes. The sensors are furthermore distinguished by a high storage stability.

Preferably, the process is used for test solutions that have a pH of from 6.5 to 8.5, especially preferably a pH value of from 6.7 to 7.8.

The ionic strength of the test solution is preferably from 0.05 to 5 mol/l, especially preferably from 0.05 to 1 mol/l.

The test solution may comprise salts of inorganic or organic acids. Examples are salts of citric acid, lactic acid or acetic acid or also salts of phosphoric acid, hydrochloric acid and sulfuric acid, or carbonate.

Preferably, the test solution comprises essentially 1,1- or 1,2-salts. Examples of 1,1-salts are LiCl, NaCl, KCl and $NH_4Cl$. Examples of 1,2-salts are $CaCl_2$, $MgCl_2$ and $K_2SO_4$ as described, for example, in G. Kortüm, Lehrbuch der Elektrochemie, 4th edition, Verlag Chemie 1966, page 156.

Preferably, the test solution consists partly or wholly of a body fluid. Especially preferably it consists partly or wholly of blood.

The process can be performed as a single measurement or can be performed continuously.

The invention relates also to the use of an optical sensor described above for the ionic strength-independent optical determination of the pH value of an aqueous test solution according to the fluorescence method.

The following Examples illustrate the invention.

EXAMPLE A
Preparation of the Functionalised Fluorescent Dyes

EXAMPLE A1
Preparation of 4-acryloylamidofluorescein (101)

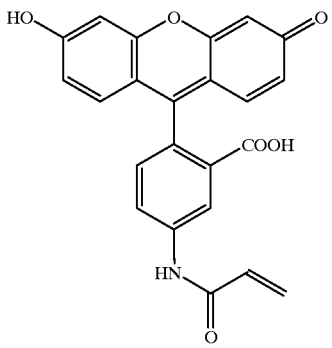
(101)

5 g of 4-aminofluorescein are suspended in 200 ml of acetone and, at 0° C., 1.4 ml of acryloyl chloride in 2 ml of acetone are added dropwise in the course of 10 min. The suspension is stirred for 3 hours at room temperature. The crystals are filtered off, washed with acetone and ether and dried. 5.7 g of compound (101) having a melting point of >200° C. are obtained. MS-FD: 402.

EXAMPLE A2
Preparation of Compound (102)

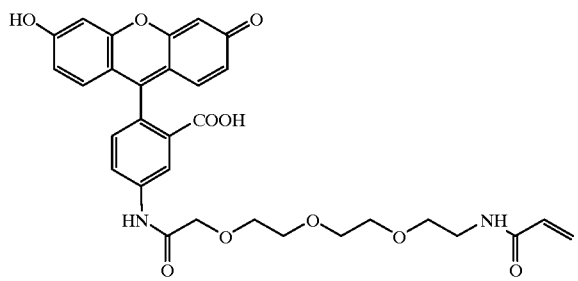
(102)

a)

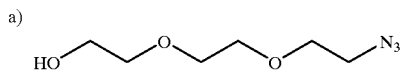
(103)

29 ml of triethylene glycol monochlorohydrin and 20 g of sodium azide are stirred overnight at 110° C. without solvent. The reaction mixture is diluted with ether and filtered off. The solvent is evaporated and the filtrate is concentrated under a high vacuum at 110–115° C. Compound 103 is obtained in a yield of 86%.

b)

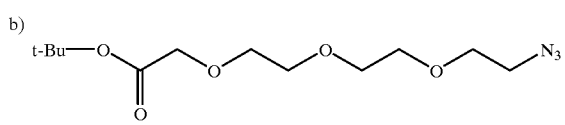
(104)

8.2 g of NaH (washed with pentane) are suspended in 150 ml of dry tetrahydrofuran. 30 g of compound (103) are added dropwise at 5° C. The mixture is stirred for a further 30 min. and subsequently reacted with 38 ml of α-bromoacetic acid tert-butyl ester in 60 ml of tetrahydrofuran. The mixture is stirred overnight, the ether is evaporated and the organic phase is washed three times with water and once with salt solution and then dried. The oil which remains is distilled under a high vacuum at from 140 to 150° C. Compound (104) is obtained. FAB-MS: 290 [M+H]$^+$. $^1$H-NMR (CDCl$_3$): 1.45 ppm (9H, s, t-Bu); 4.03 (2H, s, OCH$_2$COO).

c)

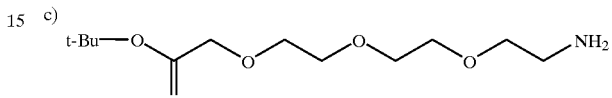
(105)

The azide group of compound (104) is quantitatively reduced with hydrogen, 5% Pd/C being used as catalyst and 1,4-dioxane being used as solvent. Compound (105) is obtained. $^1$H-NMR (CDCl$_3$): 1.45 ppm (9H, s, t-Bu); 2.2 (2H, broad, NH$_2$); 2.9 (2H, t, J=6 Hz, CH$_2$N); 4.03 (2H, s, OCH$_2$COO).

d)

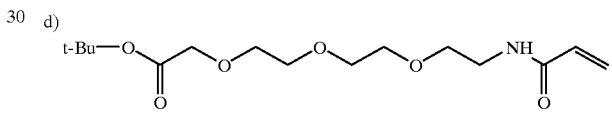
(106)

Compound (105) is dissolved in CH$_2$Cl$_2$ and treated with 1.5 equiv. of NEt$_3$ and 1.5 equiv. of acryloyl chloride at 0° C. The clear solution is stirred for 5 hours, and then washed with water, salt solution and water. The organic phase is dried. The oil which remains is purified by chromatography on silica gel with CH$_2$Cl$_2$ as eluant. The yield is 74% of compound (106). $^1$H-NMR (CDCl$_3$): 1.45 ppm (9H, s, t-Bu); 4.03 (2H, s, OCH$_2$COO); 5.10 (1H, m, CH=C); 6.05–6.35 (2H, m, C=CH$_2$).

e)

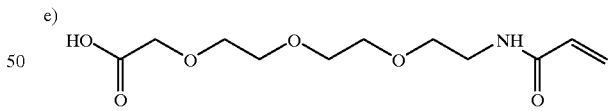
(107)

The tert-butyl ester of compound (106) is removed with a 1:1 mixture of trifluoroacetic acid and CH$_2$Cl$_2$ at room temperature in the course of 6 hours. The reaction product (107) is used directly for the next step without being purified.

f) The acid (107) is treated with one equivalent of carbonyldiimidazole in tetrahydrofuran for 3 hours at room temperature. 0.9 equivalent of 4-aminofluorescein in tetrahydrofuran is added to that solution and the mixture is stirred for 72 hours at room temperature. The reaction mixture is dried and the product is purified by chromatography on silica gel using MeOH/CH$_2$Cl$_2$ as eluant. Orange crystals of compound (102) are obtained in a yield of 37%

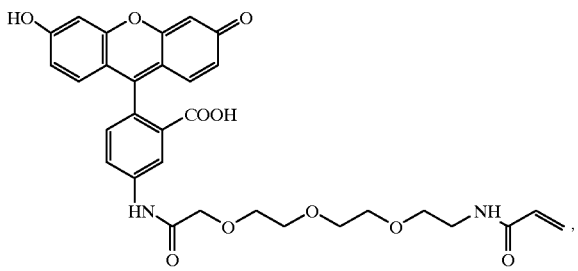

(102)

with a melting point of 205° C. (decomposition). FAB-MS: 591 [M+H]⁺, 613 [M+Na]⁺, 629 [M+K]⁺.

B Preparation of the copolymers

EXAMPLE B1

In an ampoule provided with a 3-way tap, which is connected to a vacuum and nitrogen, 2.19 g (22.1 mmol) of N,N dimethylacrylamide, 2.81 g (22.1 mmol) of N-tert-butylacrylamide, 200 mg of 4-acryloylamidofluorescein (compound 101 from Example A1) and 25 mg of azobisisobutyronitrile are dissolved in 15 ml of dimethyl sulfoxide. The atmosphere in the ampoule is replaced with nitrogen by a freeze/thaw cycle carried out three times. The ampoule is maintained at 60° C. for 2 days in a water bath. The viscous contents of the ampoule are diluted with 100 ml of warm methanol and the copolymer is precipitated by cautiously pouring dropwise into 2 l of water with stirring. The copolymer is filtered, and roughly dried. The precipitation is repeated twice more. The thus purified end product is dried under a high vacuum at 600.

Yield: 3.6 g or 69% of the theoretical yield, glass transition temperature $T_g$=156° C., content of N-tert-butylacrylamide=45.7% by weight (determined by IR-spectroscopy), inherent viscosity of a 0.5% solution in chloroform at 25° C. $\eta_{inh}$=1.07 dl/g.

EXAMPLE B2

The procedure is as in Example B1 except that 125 mg of the fluorescent dye (101) from Example A1 are added. A copolymer having the following characteristics is obtained. Yield 4.4 g or 86% of the theoretical yield, $T_g$=152° C., content of N-tert-butylacrylamide=54.2% by weight (determined by IR-spectroscopy), inherent viscosity of a 0.5% solution in chloroform at 25° C. $\eta_{inh}$=1.39 dl/g, dye content determined by UV-spectroscopy=2.2% by weight.

EXAMPLE B3

The procedure is as in Example B1 except that 15 mg of the fluorescent dye (101) from Example A1 are added. A copolymer having the following characteristics is obtained. Yield 3.4 g or 68% of the theoretical yield, $T_g$=149° C., content of N-tert-butylacrylamide=58.7% by weight (determined by IR-spectroscopy), inherent viscosity of a 0.5% solution in chloroform at 25° C. $\eta_{inh}$=1.68 dVg, dye content determined by UV-spectroscopy=0.26% by weight.

EXAMPLE B4

In an ampoule provided with a 3-way tap, which is connected to a vacuum and nitrogen, 2.19 g (22.1 mmol) of N,N-dimethylacrylamide, 2.81 g (22.1 mmol) of N-tert-butylacrylamide, 35 mg of compound 162 from Example A2 and 25 mg of azobisisobutyronitrile are dissolved in 15 ml of dimethyl sulfoxide. The atmosphere in the ampoule is replaced with nitrogen by a freeze/thaw cycle carried out three times. The ampoule is maintained at 60° C. for 5 days in a water bath. The viscous contents of the ampoule are diluted with 25 ml of warm methanol and the copolymer is precipitated by cautiously pouring dropwise into 1.5 l of ether with stirring. The copolymer is filtered, and roughly dried. The precipitation is repeated twice more. The thus purified end product is dried under a high vacuum at 50° for 2 days.

Yield: 4.05 g or 81% of the theoretical yield, glass transition temperature $T_g$=151° C., content of N-tert-butylacrylamide=51.9% by weight (determined by IR-spectroscopy), inherent viscosity of a 0.5% solution in tetrahydrofuran at 25° C. $\eta_{inh}$=1.34 dl/g, dye content determined by UV-spectroscopy=0.44%.

EXAMPLE B5

The procedure is as in Example B4 except that 2.31 g (23.29 mmol) of N,N-dimethylacrylamide, 2.69 g (19.06 mmol) of N-methyl-N-butylacrylamide and 35 mg of the fluorescent dye (101) from Example A1 are added.

A copolymer having the following characteristics is obtained. Yield 3.72 g or 74% of the theoretical yield, $T_g$=90° C., content of N,N-dimethylacrylamide=55.7 mol % (determined by IR-spectroscopy), inherent viscosity of a 0.5% solution in chloroform at 25° C. $\eta_{inh}$=1.17 dl/g, dye content determined by UV-spectroscopy=0.62% by weight.

C Production of the Sensors

EXAMPLE C1

Glass substrates (platelets of 18 mm diameter) are first of all cleaned in 30% sodium hydroxide solution and then activated in 65% nitric acid. The activated platelets are then silanised with 3-aminopropyltrimethoxysilane. The silanised platelets are left to react for 1 hour at room temperature in a solution of O—(N-succinimidyl)-6-(4'-azido-2'-nitrophenylamino)-hexanoate in dimethylformamide/borax buffer (5:1). The polymer of Example B1 (5%) is dissolved in methanol at from 200 to 250 and applied in the form of a thin film, by spin-coating at a speed of 500 revs/min for 20 seconds, onto the platelets functionalised with azido groups, irradiated for 15 min. and then dried for 12 h at 60° under nitrogen. The layer thicknesses of the membranes are approximately 1 μm.

EXAMPLES C2 TO C5

Procedure is as in Example C1 and the corresponding polymers of Examples B2 to B5 are used.

D Application Examples

General method

The sensors are mounted in a flow cell. The calibration and sample solutions are metered by pumps and conveyed through the cell. The measuring arrangement is thermostatically controlled. The light of a halogen lamp (white light, excitation wavelength 480 nm) is conducted through an excitation filter and reflected at a dichroic mirror and focussed by lenses onto the planar sensors. The fluorescent light emitted by the sensors (at 520 nm) is collected by the same lens system and directed by an emission filter and the dichroic mirror to a photodiode. The fluorescence of the sensors is recorded while they are being acted upon by the calibration and sample solutions. The pH value can be determined directly from the measured value.

The following Table 1 illustrates the dependence of the pH on the ionic strength of the electrolyte in the pH range of from 6.7 to 8.0 that results on the basis of the different membrane compositions.

TABLE 1

| Sensor from Example | Amount of dye | $pK_a$ at ionic strength 0.1 mol/l | Ionic strength dependence at 0.1 and 0.3 mol/l |
|---|---|---|---|
| C1 Comparison test. | 4% by wt. | not determinable | very high (>1)[1] |
| C2 Comparison test | 2.2% by wt. | 7.3 | high (1)[1] |
| C3 | 0.26% by wt. | 7.3 | independent (0)[1] |
| C4 | 0.44% by wt. | 7.3 | independent (0)[1] |
| C5 | 0.62% by wt. | 7.5 | independent (0)[1] |

[1]The numerical values relate to the difference between the $pK_a$ values, which were measured once at an ionic strength of 0.1 mol/l and once at an ionic strength of 0.3 mol/l.

What is claimed is:

1. A water-insoluble copolymer which is composed of
   a) from 39.9 to 60% by weight of N,N-dimethylacrylamide or N,N-dimethyl methacrylamide;
   b) from 60 to 39.9% by weight of a monomer of formula Ia or Ib

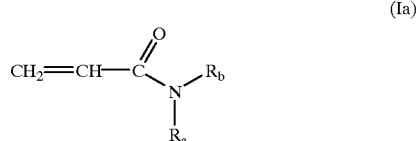

(Ia)

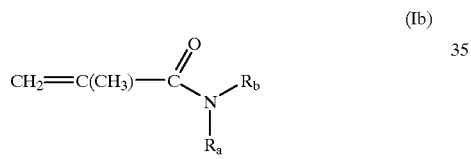

(Ib)

wherein $R_a$ is hydrogen or $C_1$–$C_6$alkyl and $R_b$ is $C_1$–$C_{12}$alkyl; with the proviso that $R_a$ and $R_b$ are not both methyl;

c) from 0.1 to 0.7% by weight of a proton-sensitive fluorophore selected from the group consisting of acridines, acridones, rhodamines, xanthenes, benzoxanthenes, pyrenes and coumarins, which is covalently bonded to the copolymer; and
   d) from 0 to 20% by weight of a diolefinic crosslinking component, the sum of the percentage weights of a) to d) being 100%.

2. A water-insoluble copolymer according to claim 1, wherein N,N-dimethylacryl amide is used as monomer a).

3. A water-insoluble copolymer according to claim 1, wherein $R_a$ is hydrogen and $R_b$ is a branched $C_3$–$C_8$alkyl.

4. A water-insoluble copolymer according to claim 3, wherein $R_a$ is hydrogen, $R_b$ is tert-butyl and the ratio of monomer a) to monomer b) is 50 parts by weight to 50 parts by weight.

5. A water-insoluble copolymer according to claim 1, wherein $R_a$ is methyl or ethyl and $R_b$ is linear $C_3$–$C_8$alkyl.

6. A water-insoluble copolymer according to claim 5, wherein $R_a$ is methyl and $R_b$ is n-butyl.

7. A water-insoluble copolymer according to claim 1, wherein the fluorophore is a compound of formula II, III, IV, V or VI

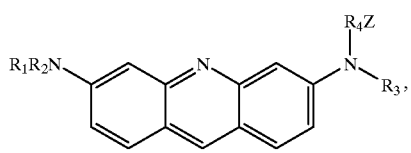

(II)

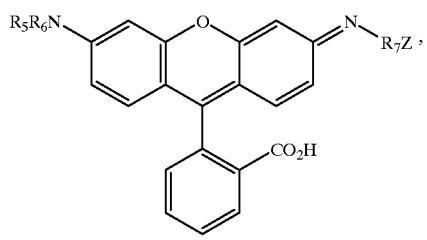

(III)

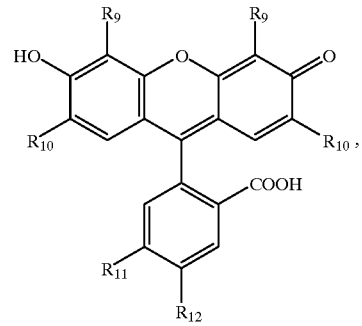

(IV)

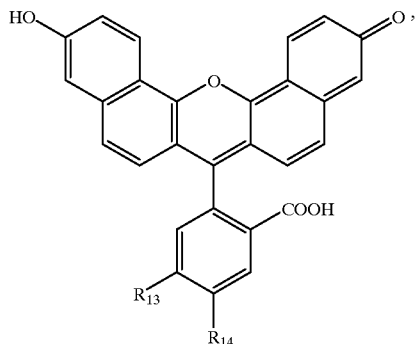

(V)

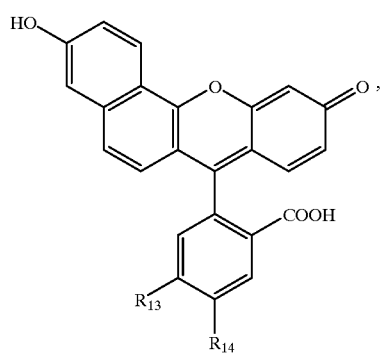

(VI)

where
$R_1$, $R_2$, $R_5$ and $R_6$ are each independently of the others hydrogen, —$SO_2$—($C_1$–$C_6$)alkylphenyl, $C_1$–$C_{30}$alkyl, $C_1$–$C_{30}$alkyl-CO— or a radical of the formula —($C_nH_{2n}$—O—$)_m$—$R_8$;
$R_3$ is hydrogen or —$SO_2$—($C_1$–$C_6$)alkylphenyl;

$R_4$ and $R_7$ are a $C_1$–$C_{30}$alkylene or a radical of the formula —$(C_nH_{2n}$—O—$)_m$—$R_8$;

Z is a divalent radical —NH—CO—;

$R_8$ is a direct bond or $C_1$–$C_{12}$alkylene;

n is an integer from 2 to 6 and m is an integer from 1 to 10, with the proviso that the total number of carbon atoms is no more than 30;

$R_9$ and $R_{10}$ are each independently of the other H, $C_1$–$C_4$alkyl, $C_1$–$C_4$alkoxy, $C_1$–$C_4$alkoxycarbonyl, $C_1$–$C_4$alkyl-$SO_2$— or halogen, and either $R_{11}$ is H and $R_{12}$ is a divalent radical —NH—CO—, —CO—NH—($C_2$–$C_{12}$alkylene-O)—CO—, —CO—NH—($C_2$–$C_{12}$alkylene-NH)—CO— or —C(O)—NH—($CH_2CH_2$-O)$_1$ to $_6$-$CH_2C(O)$—NH—, or $R_{11}$ is a divalent radical —NH—CO—, —CO—NH—($C_2$–$C_{12}$alkylene-O)—CO—, —CO—NH—($C_2$–$C_{12}$alkylene-NH)—CO— or —C(O)—NH—($CH_2CH_2$-O)$_1$ to $_6$-$CH_2C(O)$13 NH—, and $R_{12}$ is H; or wherein either $R_{13}$ is H and $R_{14}$ is a divalent radical —NH—C(O)—, —CO—NH—($C_2$–$C_{12}$alkylene-O)—CO—, —CO—NH—($C_2$–$C_{12}$alkylene-NH)—CO— or —C(O)—NH—($CH_2CH_2$—O)$_1$ t, $_6$-$CH_2C(O)$—NH—, or $R_{13}$ is a divalent radical —NH—C(O)—, —CO—NH—($C_2$–$C_{12}$alkylene-O)—CO—, —CO—NH—($C_2$–$C_{12}$alkylene-NH)—CO— or —C(O)—NH—($CH_2CH_2$—O)$_1$ to $_6$-$CH_2C(O)$—NH—, and $R_{14}$ is H, wherein the radical —COOH is each in free form or in salt form, or a $C_1$–$C_{20}$alkyl ester thereof.

8. A water-insoluble copolymer according to claim 7, wherein $R_1$ and $R_2$ of the fluorophore of formula 11 are each independently of the other hydrogen or linear $C_{12}$–$C_{24}$alkyl.

9. A water-insoluble copolymer according to claims wherein $R_4$ of the fluorophore of formula II is a linear $C_2$–$C_{16}$alkylene or a radical of the formula —($C_2H_4$—O—$)_m$—R8 wherein $R_8$ and m are as defined in claim 9.

10. A water-insoluble copolymer according to claim 7, wherein $R_5$ and $R_6$ of the fluorophore of formula III are each independently of the other linear $C_2$–$C_{12}$alkyl.

* * * * *